United States Patent [19]

Shieh et al.

[11] Patent Number: 5,620,872
[45] Date of Patent: Apr. 15, 1997

[54] HAZE-FREE CYCLODEXTRINS

[75] Inventors: Wen Shieh; Allan Hedges, both of Crown Point, Ind.

[73] Assignee: American Maize-Products Company, Hammond, Ind.

[21] Appl. No.: 479,866

[22] Filed: Jun. 7, 1995

Related U.S. Application Data

[63] Continuation of Ser. No. 792,022, Nov. 13, 1991, abandoned.

[51] Int. Cl.$^6$ ............................ C12P 19/18; C12P 19/14; C12P 19/04
[52] U.S. Cl. .............................. 435/97; 435/99; 435/101
[58] Field of Search ........................... 435/101, 97, 99

[56] References Cited

U.S. PATENT DOCUMENTS

| | | | |
|---|---|---|---|
| 3,425,910 | 2/1969 | Armsbruster et al. | 435/101 |
| 3,652,398 | 3/1972 | Armbruster | 435/101 |
| 4,028,186 | 6/1977 | Sakai | 435/97 |
| 4,418,144 | 11/1983 | Okada et al. | 536/103 |
| 4,822,874 | 4/1989 | Schmid et al. | 536/103 |
| 4,835,105 | 5/1989 | Seres et al. | 435/97 |

*Primary Examiner*—Michael G. Wityshyn
*Assistant Examiner*—Francisco C. Prats
*Attorney, Agent, or Firm*—Lucas & Just

[57] ABSTRACT

A cyclodextrin which when added to water produces a haze-free solution is made by the use of starch which contains at least about 90% amylopectin in a two-stage process wherein first a starch hydrolysate is formed by means of an alpha-amylase or an acid and a second subsequent step wherein the cyclodextrin is formed by means of a cyclodextrin-glycosyl-transferase.

19 Claims, No Drawings

HAZE-FREE CYCLODEXTRINS

This is a continuation of application Ser. No. 07/792,022, filed Nov. 13, 1991, now abandoned.

This invention relates to cyclodextrins and, more particularly, to a method for obtaining cyclodextrins which, when added to water, produce a solution which is substantially haze-free.

Cyclodextrins are oligomers of anhydroglucose which are in a ringed structure. Conventionally, cyclodextrins are formed by the action of an enzyme, cyclodextrin-glycosyl-transferase (CGTase) on starch, or a starch hydrolysate having a dextrose equivalent (DE) less than 10. Cyclodextrins are named according to the number of anhydroglucose units in the ring. The most common cyclodextrins are alpha, beta and gamma cyclodextrins which have 6, 7 and 8 anhydroglucose units in their ring structure, respectively.

Cyclodextrins, due to their ringed structure, are most noted for their ability to act as a host compound for other molecules (guest compounds). This host-guest relationship is especially important in the fields of medicine, agriculture, chemicals, foods and cosmetics.

During the treatment of starch with CGTase, acyclic material and cyclodextrins are formed. The acyclic material is, for the most part, considered to be a waste product which must be separated from the desired cyclodextrin. Methods for purifying and separating the desired cyclodextrins tend to be expensive and often involve the use of other enzymes. See, for example, U.S. Pat. Nos. 4,384,898; and 4,418,144. A breakthrough came with the discovery of the process taught in U.S. Pat. No. 4,808,232 issued Feb. 28, 1989.

A problem associated with the prior art methods of separating and purifying cyclodextrins is that aqueous solutions containing the separated and purified cyclodextrins were found to haze readily at room temperature even after extensive purification treatments. Thus, a solution which contains essentially "pure" cyclodextrins forms a haze upon standing at ambient conditions. Although in some applications such as cloudy beverages and agricultural chemicals, haze has little or no effect, in other areas such as foods and pharmaceuticals, clarity is important and haze has a deleterious effect on the marketability of the cyclodextrins.

It has now been discovered that, by employing a two-stage process for making a cyclodextrin, a cyclodextrin is produced which, when added to water, produces a solution which is substantially haze-free. The two stages of the present invention are hydrolyzing a starch having an amylopectin content of at least 90% with an acid or enzyme to form a starch hydrolysate having a dextrose equivalent (DE) below about 10; and converting the starch hydrolysate to cyclodextrin using cyclodextrin-glycosyl-transferase. The starch must comprise at least about 90% by weight amylopectin, based on the weight of starch. More preferably, the amount of amylopectin is about 95% or above. Good results have been obtained using a starch containing about 99% amylopectin.

Good results have also been found where the starch hydrolysate is subject to a refining step prior to treatment with cyclodextrin-glycosyl-transferase. The refining step comprises bleaching the starch hydrolysate with carbon and then treating the bleached hydrolysate with an ion exchange column. The refined hydrolysate can be dried prior to treatment with the second enzyme. The drying step removes moisture from the hydrolysate to provide a dry, powdery product.

It has been found that when using the process of the present invention a solution of alpha cyclodextrin has a 90% transmittance or better; a solution of beta cyclodextrin has a transmittance of 95% or better; and a solution of gamma cyclodextrin has a transmittance of 97% or better, each solution being measured at 20% solids by weight, at ambient conditions, 20°–25° C., through a 1 cm cell at 660 nm with a spectrophotometer. It will be appreciated that in order to obtain 20% solutions of alpha and beta cyclodextrins, the solution must be heated in order to get such a high solids level. It will also be appreciated that after cooling the solutions of alpha and beta cyclodextrins prior to measurement that some of the cyclodextrin will crystalize out and rest on the bottom of the test tube.

It is not known why using a starch base high in amylopectin, 90% and above, causes the resulting cyclodextrins to produce a solution which is substantially haze-free. It is not known what is in solution besides cyclodextrin nor what causes the haze. It is suspected that the cyclodextrin itself does not cause the haze but rather the other chemicals which are present in solution. These other chemicals may be made up of anhydroglucose; however, their specific structure is not known. They may simply be acyclic dextrins which have passed with the cyclodextrin through the refining process.

Broadly, the process of the present invention entails first treating an aqueous slurry of starch with either an acid or an enzyme to form a starch hydrolysate followed by a second step of treating the starch hydrolysate with cyclodextrin-glycosyl-transferase to form cyclodextrin. In order to form the starch hydrolysate, an aqueous slurry of starch is formed wherein said starch has an amylopectin content above about 90% by weight based on the weight of the starch. The starch is then gelatinized by subjecting the slurry to heat and agitation. Next, the gelatinized starch is liquefied to produce a starch hydrolysate having a DE below about 10. Preferably, the starch hydrolysate is next bleached with carbon. The hydrolysate can be dried to a moisture content of about 12% or less.

In order to form the cyclodextrin from the starch hydrolysate, the starch hydrolysate is treated with cyclodextrin-glycosyl-transferase (CGTase) to produce cyclodextrin, and the cyclodextrin is recovered. The recovered cyclodextrin when added to water has been found to produce a solution which is substantially free of haze.

The DE of the starch hydrolysate is measured in any known acceptable manner; Lane-Eynon is preferred. More preferably, the starch hydrolysate has a DE of about 1 to about 8. Good results are obtained with a starch hydrolysate having a DE of about 5.

Starch is essentially made up of two types of polymers of anhydroglucose. One type of polymer is generally referred to as amylose and consists of anhydroglucose monomers linked together by alpha 1,4 bonds. The other polymer is referred to as amylopectin and consists of anhydroglucose monomers linked together by both alpha 1,4 and alpha 1,6 bonds. Generally, alpha 1,6 bonds are fewer in number than alpha 1,4 bonds in amylopectin.

The starch used in the present invention has an amylopectin content at least about 90%, and, more preferably, about 95% and above. Good results have been obtained with a starch having about 99% amylopectin. Suitable starches for this process are waxy maize, waxy rice and waxy barley. Waxy maize is the preferred source.

In order to form a starch slurry in accordance with the present invention, starch granules are added to water to form a suspension having a solids content of about 5% to about 50% by weight and, more preferably, about 10% to about 40% by weight. More preferred is to operate at about 20% to about 40% by weight.

Prior to liquefaction, the starch slurry is subjected to a gelatinization step. The gelatinization process disrupts, in whole or in part, the associative bonding of the starch molecules within the raw starch granule, thereby making the molecules more accessible to uniform liquefaction. The gelatinization step is conducted in a conventional manner using conventional equipment. Gelatinization is conventionally conducted by subjecting a slurry of starch granules to heat at a temperature above the gelatinization temperature of the starch while subjecting the starch to constant agitation.

Liquefaction is conducted in a conventional manner using conventional equipment. Typically, a jet cooker is used for this process. Usually gelatinization and liquefaction are performed simultaneously in the jet cooker. In such cases, the enzyme or acid used for liquefying the starch is added during the formation of the slurry. The enzyme used for liquefaction is an alpha-amylase and preferably a bacterial alpha-amylase. Treatment with the enzyme is conducted at the optimum concentration, pH and temperature for the specific enzyme employed. Specifically, treatment with bacterial alpha-amylase is conducted at about 60° to about 100° C., preferably about 80° C., at a pH of about 5 to about 8, preferably about 5.5, for a period of time sufficient to form the starch hydrolysate in the desired DE range. The action of the alpha-amylase is stopped by inactivating the enzyme by heating to about 120° C. or above or by the addition of acid. Once the enzyme has been inactivated, the pH is readjusted to about 5 to about 8 prior to the next step. It is preferred that the enzyme be inactivated by heating and specifically by jet cooking the slurry at a temperature of about 110° C. to inactivate the bacterial alpha-amylase.

The acid treatment is conducted by heating the slurry of starch granules to about 100° to about 120° C. in the presence of a mineral acid such as hydrochloric, sulfuric or nitric acid for a period of time sufficient to raise the DE of the slurry to the desired range. For both the enzymatic and acid treatments, the starch slurry has a solids content of about 5% to about 40% solids, more preferably about 30 to about 35%.

Preferably, after formation of the hydrolysate, the hydrolysate slurry is treated with carbon and an ion exchange resin to refine the hydrolysate.

Carbon treatment of the starch hydrolysate slurry is accomplished using activated carbon to remove color, color precursors, and undesirable off-flavored materials. Carbon treatment removes most of the soluble proteinaceous material present and substantially all the 5-(hydroxymethyl)-2-furaldehyde formed during the acid treatment. Additionally, activated carbon is effective in the removal of heavy metals, such as iron and copper. Conventionally, carbon treatment is a 2- or 3-stage countercurrent batch application of activated powdered carbon or a countercurrent application of activated granular carbon in cylindrical columns. Such operation is accomplished in a conventional manner.

Although carbon refining is adequate for purification of most conventional starch hydrolysate slurries, it is preferred to further treat the slurry by ion-exchange deionizer. Such treatment removes substantially all remaining soluble nitrogenous compounds, including amino acids and peptides that contribute color body formation via the Maillard reaction with reducing sugars.

A typical ion-exchange deionization system consists of fixed-bed columns. The cation-exchange resins used are strong acid exchangers (sulfonated resins in the hydrogen form), and the anion exchangers usually are weak base resins (tertiary amine in the free base form). The anion-exchange resins remove acids generated by reaction of the salts in the syrup liquor with the cation-exchange resins.

After refining the starch hydrolysate, the starch hydrolysate can be dried to a moisture level of about 15% or less. More preferably, the moisture content of the starch hydrolysate is about 5% or less. Drying is accomplished in a conventional manner by first concentrating the slurry and then subjecting the concentrated slurry to a final drying step such as by drum drying, spray drying or freeze drying. The dried, refined starch hydrolysate is then stored until the second stage of the process of the present invention.

In the second stage of the present invention, an aqueous slurry of starch hydrolysate is treated with CGTase at the optimum concentration, pH and temperature for the CGTase employed for forming the cyclodextrins. Formation of the cyclodextrin by CGTase is done in a conventional manner using conventional equipment. Conventionally, a temperature of about 30° to about 100° C. is employed for a period of time sufficient to form cyclodextrin. Conventionally, the pH of the aqueous slurry of starch hydrolysate is maintained at about 4 to about 7 and the treatment is conducted for about four to about forty-eight hours. When CGTase from *B. macerans,* alkalophilic Bacillus Sp. or Thermoanaerobacter Sp. are used, the concentration of the refined starch hydrolysate slurry is suitably about 5% to about 20% solids based on total weight of the solution. Preferably, the starch hydrolysate has a concentration of about 10% to about 20% by weight and, more preferably, about 15% by weight. Formation of cyclodextrin by CGTase may also be conducted in the presence of a complexant. This is done in a conventional manner using conventional equipment. The use of complexant in the formation of cyclodextrin is typically referred to as the solvent process. The concentration of the starch hydrolysate in the solvent process is suitably about 5 to about 50% solids based on total weight of the solution. Preferably, the starch hydrolysate slurry has a concentration of about 10 to about 40% by weight and, more preferably, about 20 to about 40% by weight. In the solvent process the treatment time is between about 4 hours to about 4 days. Suitable complexants are toluene, 1-decanol, cyclohexane, trichloroethylene, tetrachloroethane, bromobenzene, 2,3-cyclododecenopyridine, naphthalene, 1-naphthol, 2-naphthol, and dimethylphenol. The preferred complexants are cyclohexane, toluene, 1-decanol and 2,3-cyclododecenopyridine. Suitable enzyme sources for CGTase include *B. macerans,* alkalophilic Bacillus Sp. and Thermoanaerobacter Sp. Such enzymes are conventional and available through conventional sources. The cyclodextrin-glycosyl-transferase can be thermostable.

After treatment with CGTase enzyme, by either the solvent or non-solvent process, the cyclodextrin must be recovered. When a complexant is not used, the enzyme is inactivated and the solution is preferably treated with an enzyme to degrade the remaining starch hydrolysate to glucose and/or maltose. Good results have been obtained by heating the solution to a temperature of about 130° C. and holding the solution at that temperature for about 5 to about 10 minutes to inactivate the enzyme. To form the glucose/maltose, good results have been obtained using a glucoamylase or beta-amylase at a temperature of about 50° to about 70° C. for a period of about 24 hours at a pH of about 4 to about 6.

Next, the reaction mixture is filtered, carbon treated and the supernatant is evaporated to form beta cyclodextrin crystal. The mother liquor is passed through a chromatographic column of the type taught by U.S. Pat. No. 4,808,232 to separate the different cyclodextrins from each other, i.e. alpha, beta and gamma.

In the case of a complexant, after treatment with CGTase to form the cyclodextrins, the complex of cyclodextrin and complexant are recovered, preferably by centrifugation or by filtration and the resulting complex is treated to remove the complexant. Distillation or solvent extraction are the preferred means to remove the complexant. The solution of cyclodextrin is then treated with activated carbon and the cyclodextrin is subsequently recovered, preferably by crystallization.

Carbon treatment of the cyclodextrin in solution is accomplished using activated carbon to remove color, color precursors, and undesirable off-flavored materials. Carbon treatment is a batch application of activated powdered carbon or a counter-current application of activated granular carbon in cylindrical columns. Such operation is accomplished in a conventional manner.

These and other aspects of the present invention may be more fully understood by reference to the following examples:

EXAMPLE 1

This example illustrates the superior results of the present invention. Table I below illustrates the percent transmittance measured for cyclodextrin solutions made from a waxy corn starch (99% amylopectin), a common corn starch (70% amylopectin) and potato starch (80% amylopectin).

TABLE I

|          | Waxy Corn Starch (% T) | Potato Starch (% T) | Common Corn Starch (% T) |
|----------|------------------------|---------------------|--------------------------|
| Alpha-CD | 98.2                   | 81.3                | 35.8                     |
| Beta-CD  | 99.4                   | 92.8                | 61.8                     |
| Gamma-CD | 99.3                   | 95.3                | 64.8                     |

Each solution was measured at 20% solids by weight, at ambient condition, 20°–25° C., through a 1 cm cell at 660 nm with a spectrophotometer (Beckman Instruments Inc.). In order to obtain a 20% solution of the alpha and beta cyclodextrin, the solution must be heated initially to about 50° C. and about 80° C., respectively. After cooling the solutions of alpha and beta cyclodextrin prior to measurement, some of the cyclodextrin crystallized out and rested on the bottom of the test tube.

In order to obtain the measurements in Table I above, twenty percent (20%) solutions of each cyclodextrin were made by heating the solution. Then the solution was allowed to cool to ambient temperature. Gamma cyclodextrin was measured after cooling, while the percent transmittance of alpha and beta cyclodextrin solutions were measured after crystallization of the cyclodextrin and filtration through Whatman #1 filter paper to remove crystals.

As can be seen from Table I above, the cyclodextrin produced from a starch high in amylopectin, above about 90% by weight, produced superior results to cyclodextrin produced from starch having lesser amounts of amylopectin.

In order to form the cyclodextrins from the waxy corn starch, a slurry of waxy corn starch was formed at 30% solids and subjected to gelatinization and subsequently to liquefaction by treating the slurry with alpha-amylase to form a waxy starch hydrolysate having a DE of about 5. The waxy starch hydrolysate (30% solids) was then treated with a CGTase from *B. macerans* at a temperature of 60° C. for 4 days. During the formation of the cyclodextrins, a complexant of 1-decanol was used to obtain alpha cyclodextrin. Toluene was used as a complexant for beta cyclodextrin and 2,3-cyclododecenopyridine was used as a complexant for gamma cyclodextrin. The different complexants were added to the solution in an amount equal to 5% of reaction volume at the start of the treatment with the CGTase. In order to remove the complexant from the cyclodextrin, solvent extraction and distillation were employed.

To form cyclodextrins from common corn starch, the same process used in the waxy starch was employed except the slurry of starch was 15% solids not 30% solids.

In order to make cyclodextrins from potato starch, a slurry of potato starch at 15% solids was formed and treated to the same gelatinization and liquefaction steps as the waxy and common corn starch. CGTase from *B. macerans* was employed at a temperature of 50° to 60° C. for a period of 2 days to form cyclodextrins.

It will be understood that the claims are intended to cover all changes and modifications of the preferred embodiment of the invention herein chosen for the purpose of illustration which do not constitute a departure from the spirit and scope of the invention.

What is claimed is:

1. A process for making a cyclodextrin, which, when added to water, produces a substantially haze-free solution comprising the successive steps of:

(a) selecting a starch having an amylopectin content of at least about 90%;

(b) forming an aqueous starch slurry with said starch;

(c) treating said starch slurry with an alpha-amylase or an acid to hydrolyze said starch and form a starch hydrolysate having a DE of less than about 10;

(d) treating said starch hydrolysate with carbon to form a bleached starch hydrolysate;

(e) forming an aqueous slurry from the bleached starch hydrolysate;

(f) treating said bleached starch hydrolysate slurry with a cyclodextrin-glycosyl-transferase to form a cyclodextrin;

(g) recovering said cyclodextrin; and (h) treating said cyclodextrin with carbon to form a bleached cyclodextrin which, when added to water, produces a substantially haze-free solution.

2. The process of claim 1 wherein said starch is obtained from waxy maize.

3. The process of claim 1 wherein said starch slurry of step (b) is treated with alpha-amylase and said alpha-amylase is bacterial alpha-amylase.

4. The process of claim 1 wherein said cyclodextrin-glycosyl-transferase is thermostable.

5. The process of claim 1 wherein said aqueous starch slurry has a solids content of about 20% to about 40% by weight.

6. The process of claim 1 wherein said DE of said starch hydrolysate is about 5.

7. The process of claim 1 wherein said cyclodextrin-glycosyl-transferase is selected from the group consisting of *B. macerans,* alkalophilic Bacillus Sp. and Thermoanaerobacter Sp.

8. The process of claim 1 wherein a complexant is used with said cyclodextrin-glycosyl-transferase to form said cyclodextrin, said complexant being selected from the group consisting of toluene, 1-decanol, cyclohexane, trichloroethylene, tetrachloroethane, bromobenzene, 2,3-cyclododecenopyridine, naphthalene 1-naphthol, 2-naphthol, and dimethylphenol.

9. The process of claim 8 wherein said aqueous slurry of bleached starch hydrolysate has a solids content of about 10% to about 40% by weight.

10. The process of claim 1 wherein said aqueous slurry of bleached starch hydrolysate treated with said cyclodextrin-glycosyl-transferase has a solids content of about 10% to about 20% by weight.

11. The process of claim 1 further comprising the step of treating the bleached starch hydrolysate with an ion exchange resin prior to treatment with said cyclodextrin-glycosyl-transferase.

12. The process of claim 11 wherein said starch is obtained from waxy maize.

13. The process of claim 11 wherein said starch slurry of step (b) is treated with alpha-amylase and said alpha-amylase is bacterial alpha-amylase.

14. The process of claim 11 further comprising a step of drying said bleached starch hydrolysate to a moisture content of below about 15% after said step of treating said bleached starch hydrolysate with an ion exchange resin and prior to forming said aqueous slurry of bleached starch hydrolysate.

15. The process of claim 14 wherein said starch is obtained from waxy maize.

16. The process of claim 14 wherein said starch slurry of step (b) is treated with alpha-amylase and said alpha-amylase is bacterial alpha-amylase.

17. The process of claim 16 wherein said starch is obtained from waxy maize.

18. The process of claim 17 wherein said DE of said starch hydrolysate is about 5.

19. The process of claim 1 further comprising a step of drying said bleached starch hydrolysate to a moisture content of below about 15% prior to forming said aqueous slurry of bleached starch hydrolysate.

* * * * *